(12) United States Patent
Wong et al.

(10) Patent No.: US 6,914,142 B2
(45) Date of Patent: Jul. 5, 2005

(54) SYNTHESIS OF (4-BROMOPNENYL)(4-PIPERIDYL)METHANONE-(Z)-O-ETHYLOXIME AND SALTS

(75) Inventors: George S. K. Wong, Summit, NJ (US); Jeonghan Park, Whippany, NJ (US); Weidong Tong, Mountainside, NJ (US); Ramani Raghavan, Hillside, NJ (US)

(73) Assignee: Schering Corporation, Kenilworth, NJ (US)

( * ) Notice: Subject to any disclaimer, the term of this patent is extended or adjusted under 35 U.S.C. 154(b) by 131 days.

(21) Appl. No.: 10/269,803

(22) Filed: Oct. 11, 2002

(65) Prior Publication Data

US 2003/0092731 A1 May 15, 2003

Related U.S. Application Data

(60) Provisional application No. 60/329,562, filed on Oct. 15, 2001.

(51) Int. Cl.[7] ............................................. C07D 401/06
(52) U.S. Cl. ........................ 546/192; 546/192; 546/233
(58) Field of Search ................................. 546/192, 233, 546/193

(56) References Cited

U.S. PATENT DOCUMENTS

| | | | |
|---|---|---|---|
| 4,408,054 A | 10/1983 | Strupczewski et al. | |
| 5,889,006 A | * 3/1999 | Lowe et al. | ............ 514/252.02 |
| 6,043,255 A | * 3/2000 | Lowe et al. | ................. 514/316 |
| 6,642,385 B2 | * 11/2003 | Wu et al. | .................... 546/193 |

FOREIGN PATENT DOCUMENTS

| | | |
|---|---|---|
| WO | WO 00/66559 | 11/2000 |

OTHER PUBLICATIONS

Strupczewski, et al., J. Med. Chem. 28:761–769, 1985.

* cited by examiner

Primary Examiner—Cecilia J. Tsang
Assistant Examiner—Raymond Covington
(74) Attorney, Agent, or Firm—Palaiyur S. Kalyanaraman

(57) ABSTRACT

In one embodiment, the present invention describes the synthesis of (4-bromophenyl) (4-piperidyl)methanone-(Z)—O-ethyloxime and its acid salts, and similar compounds, in high stereochemical purity.

40 Claims, No Drawings

SYNTHESIS OF (4-BROMOPNENYL)(4-PIPERIDYL)METHANONE-(Z)-O-ETHYLOXIME AND SALTS

FIELD OF THE INVENTION

This application specifically discloses a novel process to synthesize (4-bromophenyl) (4-piperidyl)methanone-(Z)—O-ethyloxime and its acid salt in high stereochemical purity. It also generically discloses a process to prepare compounds similar to the above in high stereochemical purity. The invention additionally discloses a novel acid-induced isomerization to prepare predominantly the Z-isomers of such O-ethyloximes. This application claims priority from U.S. provisional application, Ser. No. 60/329,562 filed on Oct. 15, 2001. The invention disclosed herein is related to that disclosed in the provisional patent application, Ser. No. 60/329,561 filed on Oct. 15, 2001.

BACKGROUND OF THE INVENTION (4-Bromophenyl) (4-piperidyl)methanone-(Z)—O-ethyloxime hydrochloride (Formula I) is an intermediate used in the preparation of 4-[(Z)-(4-bromophenyl) (ethoxyimino)methyl]-1'-[(2,4-dimethyl-1-oxido-3-pyridinyl)carbonyl]-4'-methyl-1,4'-bipiperidine (Formula II). The compound of Formula II is discussed in pending U.S. patent application, Ser. No. 60/329,566, filed of even date herewith.

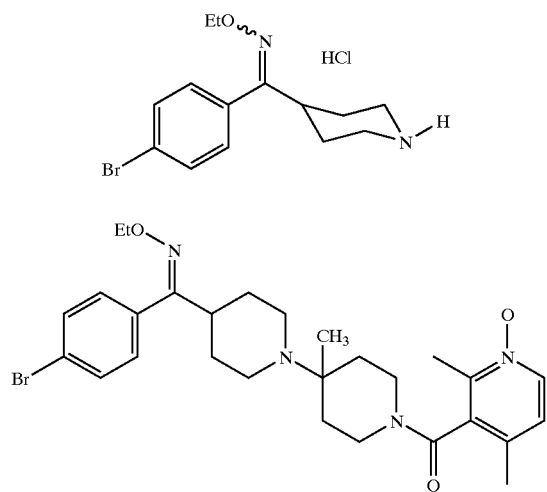

The compound of Formula II is also disclosed in the commonly owned U.S. patent application, Ser. No. 09/562,815, filed May 1, 2000. That patent application discloses several novel antagonists of the CCR5 receptor which are useful for the treatment of AIDS and related HIV infections. CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

In view of the importance of antagonists of the CCR5 receptor, new, novel methods of making such antagonists and/or their intermediates are always of interest.

SUMMARY OF THE INVENTION

In an embodiment, the present application teaches a novel, simple process of making (4-bromophenyl) (4-piperidyl)methanone-(Z)—O-ethyloxime and its acid salt in high stereochemical purity and high yields. It additionally teaches a novel, simple process to synthesize a compound of Formula I in high stereochemical purity and, via that process, a method of making a compound of Formula II in high yields and high stereochemical purity. The term "high stereochemical purity" refers to at least about 90% of the desired isomer, which, in the present invention, is the Z-isomer of the compound of Formula I. Indeed, the stereochemical purity of the compound of Formula I made by the inventive process typically exceeds 95% of the Z-isomer. The term "high yields" refers to at least about 60% yield of the desired product. The inventive process to prepare the compound of Formula I in such high stereochemical purity is also generically suitable for making compounds structurally similar to the compound of Formula I.

Thus, the present process comprises synthesizing a compound of the general Formula VII from commercially available isonipecotic acid (Formula III):

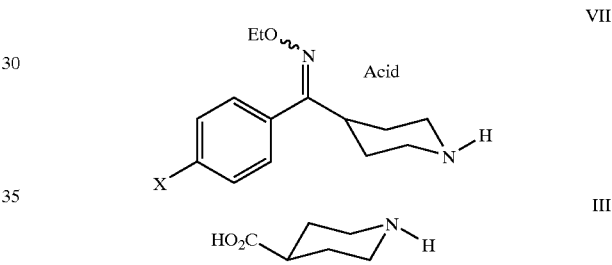

The process of making a generic compound of the type of Formula VII from a compound of Formula III comprises:

(a) preparing the N-protected derivative (Formula IIIA) from isonipecotic acid (Formula III):

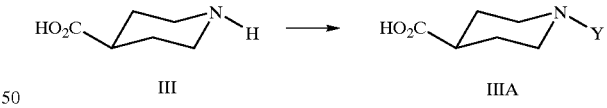

where Y is a protecting group;

(b) converting the compound of Formula IIIA to its acid halide (Formula IV):

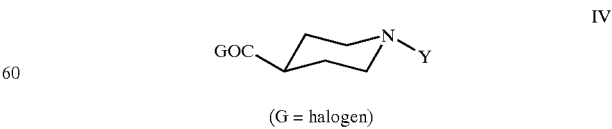

(G = halogen)

(c) reacting said compound of Formula IV with a suitable halobenzene in the presence of a suitable Friedel-Crafts catalyst to yield the compound of Formula V:

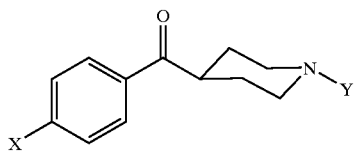

where X is a halogen derived from said halobenzene;

(d) reacting the compound of Formula V with (a) a suitable alkoxyamine and (b) an acid followed by deprotection under basic conditions to provide the compound of Formula VI as a mixture of the Z and E isomers:

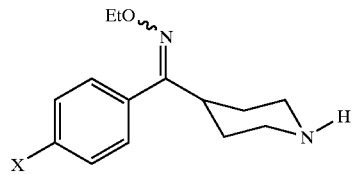

and (e) isomerizing the compound of Formula VI by treatment with a strong acid and simultaneously converting to the desired acid salt of Formula VII with an enriched Z isomer, wherein the Z isomer predominates over the E-isomer by at least a 90:10 ratio. The thus-obtained acid salt may optionally be converted to its free base by treatment with an appropriate base as one skilled in the art can appreciate.

The inventive process to make the compound of Formula VII has several advantages: it is economical, can be easily scaled-up and yields the desired Z-isomer in high yields and in high stereochemical purity.

DESCRIPTION OF THE INVENTION

In one embodiment, the present invention discloses a novel, easy-to-use process for preparing the compound of Formula VII in high yields and high stereochemical purity. When X is Br and "Acid" is HCl in Formula VII, the compound is the same as the compound of Formula I, which is an intermediate useful in the preparation of the compound of Formula II, as disclosed in pending U.S. patent application, Ser. No. 10/269,822, filed of even date herewith. The inventive process to prepare the compound of Formula VII is schematically described below in Scheme I:

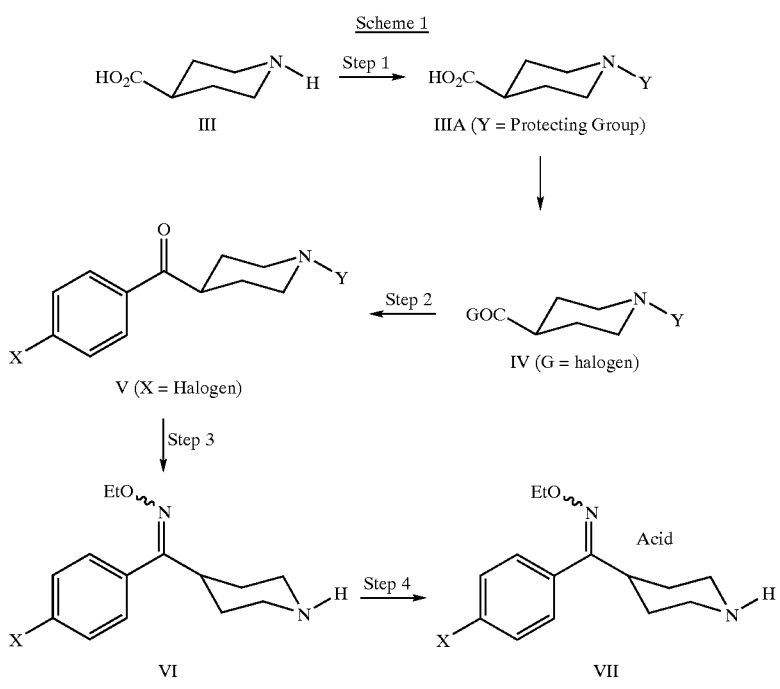

The compounds of the Formula VI and VII, and their isomers, are believed to be novel compounds. The identity of the moiety X in the Formulas V, VI and VII is the same. As stated above, the pure Z-isomer acid salt (Formula VII) may optionally be treated with an appropriate base and converted to the free base of the Formula:

Step 4 in Scheme 1 above includes a novel acid-catalyzed isomerization process to yield predominantly the Z-isomer. Preparation of syn- or anti-aminoaryl alkyl ketoximes from a mixture of isomers by acid catalysis is discussed by T. Zsuzsanna et al, *Hung.Magy.Km.Foly.*, 74(3) (1968), 116–119. The Z- and E-isomeric forms of [R-(Z)]-1-azabicyclo[2.2.1]heptan-3-one, O-[3-(3-methoxyphenyl)-2-propynyl]-oxime and their acid-catalyzed isomerization are discussed in U.S. Pat. No. 5,534,522. While the preferred reagents and reaction conditions for the various steps in the inventive process are described in detail in the Examples section, the following summarizes the details.

The presently disclosed process starts with the known compound of Formula III, which is commercially available isonipecotic acid. In step 1, isonipecotic acid is N-protected. The protecting group is introduced by reacting compound III with a suitable acid, acid chloride, acid anhydride, carboxylic ester, and the like, as is well known to those skilled in the art. Useful protective groups that may be employed are trifluoroacetyl (—C(O)CF$_3$), acetyl (—C(O)CH$_3$), formyl (—CHO), —C(O)OEt and the like; preferred is trifluoroacetyl, introduced by reacting with trifluoroacetic anhydride. The trifluoroacetic anhydride is employed generally in about 1 to about 5 molar equivalents (based on the moles of isonipecotic acid), preferably in about 1 to about 3 molar equivalents, and typically in about 1.5 to about 2 molar equivalents. A solvent may be employed such as, for example, hydrocarbons such as toluene, xylene and the like, halogenated hydrocarbons such as, for example, methylene chloride, ethylene chloride, chloroform, chlorobenzene and the like, esters such as, for example, ethyl acetate, n-butyl acetate, isopropyl acetate and the like, ethers such as, for example, tetrahydrofuran, diglyme and the like, ketones such as methyl ethyl ketone, methyl amyl ketone and the like, as well as mixtures of such solvents. Preferred are the esters, especially isopropyl acetate. Generally, isonipecotic acid is dissolved, suspended or dispersed in the selected solvent and trifluoroacetic anhydride is added and maintained at a temperature of about 0–30° C. for about 0.5–5 hours. After the reaction is complete, the product of Formula IIIA may be isolated by conventional processes such as, for example, neutralization of any remaining acid and solvent extraction.

The N-protected isonipecotic acid (IIIA) is then converted to its acid halide (IV) by reacting with a suitable reagent such as, for example, a thionyl halide, phosphoryl halide, oxalyl halide and the like; oxalyl halide, thionyl chloride is especially preferred. The acid halide may be employed generally in about 1 to about 4 molar equivalents, preferably in about 1 to about 3 molar equivalents, and typically in about 1 to about 1.5 molar equivalents. The thus-prepared acid halide of Formula IV is then subjected to a Friedel-Crafts alkylation with a halobenzene in Step 2. Friedel-Crafts alkylation is well known in the art of organic synthesis. Generally, the catalyst employed is typically a metal halide such as, for example, AlCl$_3$. Illustrative useful halobenzene is fluorobenzene, chlorobenzene, bromobenzene or iodobenzene, with chlorobenzene and bromobenzene being preferred. The halobenzene is employed generally in about 3–8 volumes, preferably in about 3–7 volumes and typically in about 4–6 volumes, with respect to the compound of the Formula IV. The AlCl$_3$ catalyst is generally employed in about 2–5 molar equivalents, preferably in about 2–4 molar equivalents and typically in about 2–3 molar equivalents with respect to the compound of Formula IV. Generally, the ingredients are mixed and maintained at a temperature range of 5–80° C. for about 1–5 hours. The product of Formula V after work-up is generally isolated by solvent extraction, precipitation or similar methods well known to those skilled in the art.

The compound of Formula V is then converted to an ethoxyoxime of Formula VI by reacting it with ethoxyamine (or its hydrochloride), usually in aqueous solution form. Ethoxyamine (or its hydrochloride) is employed generally in about 1 to about 4 molar equivalents, preferably in about 1 to about 3 molar equivalents, and typically in about 1 to about 2 molar equivalents. Generally, the reaction is catalyzed by a weak acid such as, for example, acetic acid, formic acid and the like, or mixtures thereof, in a solvent such as, for example, methanol, ethanol, isopropanol, n-butanol and the like, or mixtures thereof. The product of Formula VI, after work-up, is a mixture of the Z- and the E-isomers, whose ratio may be analyzed for its stereochemical make-up, using techniques well known in the art such as, for example, HPLC.

Since the desired isomer is the Z-isomer in compound VII, it would be advantageous to enrich the compound of Formula VI in the desired Z-isomer. Applicants found that treating the compound of Formula VI with a strong acid under certain reaction conditions surprisingly isomerizes the mixture of the Z and the E-isomers into predominantly the Z-isomer. Generally, the compound of Formula VI may be dissolved in a solvent such as, for example, ethanol, methanol, isopropanol, n-butanol and the like, ether such as methyl tert-butyl ether, tetrahydrofuran and the like, hydrocarbon such as, for example, heptane, hexane, toluene and the like, nitrile such as, for example, acetonitrile, benzonitrile and the like, or mixtures of such solvents. It is then treated with a strong acid such as, for example, HCl, HBr, H$_2$SO$_4$ and the like, at temperatures in the range 10 to 80° C. for about 1–80 hours. The acid is employed generally in about 1.1 to about 8 molar equivalents, preferably in about 1.1 to about 6 molar equivalents, and typically in about 2 to about 4 molar equivalents. Work-up typically forms predominantly the acid salt of the Z-isomer of the compound of Formula VII. HPLC analysis (when X=Br and the acid salt was HCl) after a typical reaction sequence as shown in the Examples section showed the presence of the Z-isomer generally in about 90% or above stereochemical purity, and typically in about 95% or above stereochemical purity. Additionally, the yields of the desired compound in such stereochemical purity was quite high, demonstrating that such isomerization reaction using a strong acid may be applicable to prepare Z-isomers of such oximes in high yields and high stereochemical purity.

The products of the various steps in the reaction schemes described herein may be isolated and purified by conventional techniques such as, for example, filtration, recrystallization, solvent extraction, distillation, precipitation, sublimation and the like, as is well known to those skilled in the art. The products may be analyzed and/or checked for purity by conventional methods such as, for example, thin layer chromatography, NMR, HPLC, melting point, mass spectral analysis, elemental analysis and the like, well known to those skilled in the art.

The following nonlimiting EXAMPLES are provided in order to further illustrate the present invention. While the EXAMPLES are described herein as the preparation of the compound of Formula I from the compound of Formula III, it will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:
HPLC=High Performance Liquid Chromatography
M.pt: melting point
NMR=nuclear magnetic resonance spectroscopy
DMSO=dimethylsulfoxide
mL=milliliters
g=grams
rt=room temperature (ambient)

Example 1

Preparation of Compound of Formula IV from a Compound of Formula III

This compound was prepared by following a procedure similar to M. F. Hibert et al., *J. Med. Chem.*, 33 (1990), 1594–1600. To a suspension of 440 g of isonipecotic Acid in 1760 mL of isopropyl acetate at 0–10° C. was added 880 mL of trifluoroacetic Acid over at least 2 h, while maintaining the temperature below 30° C. After complete addition, the reaction mixture was heated to 55–65° C. After about 2 h, the reaction mixture was cooled to about room temperature, and 1760 mL of isopropyl acetate was added. The reaction mixture was cooled to between −10° C. and 0° C., whereupon 1320 mL of water was added while maintaining the temperature below 15° C. This was followed by the addition of 1364 g of 25% sodium hydroxide solution while maintaining the temperature below 15° C. The biphasic mixture was stirred for about 3 h at room temperature. The aqueous layer was removed, and was extracted with 880 mL of isopropyl acetate. The combined isopropyl acetate solution was washed twice with 880 mL of a 15% sodium chloride solution each time. The reaction mixture was concentrated to about 1320 mL. Upon cooling, the product started to crystallize. The mixture was cooled to room temperature and 1760 mL of heptane was added. The suspension was cooled to between −5° C. and 5° C., stirred for 1 h, and then filtered. The collected solid was washed with 440 mL of heptane, and then dried under vacuum at 55–65° C. to give 613.6 g of the compound of Formula IV, mp: 113.5° C.

Example 2

Preparation of Compound of Formula V from a Compound of Formula IV

To a suspension containing 477 g of the compound of Formula IV in 1900 mL of bromobenzene was added 257 g of thionyl chloride. The reaction mixture was heated to 60–65° C. over about 1 h. After another 1–2 h, the reaction mixture was cooled to 10–15° C., whereupon 588 g of aluminum chloride was added in 5 portions. During each addition, the temperature was maintained between 10–15° C. After the addition of aluminum chloride was complete, the reaction mixture was heated to 65–70° C. over a 3 h period. After about 1 h, another 70 g of aluminum chloride was added. After about 1 h, the reaction mixture was transferred to 2370 mL of a 6 N hydrochloric acid solution pre-cooled to between 5° C. and 10° C. During the transfer, the temperature was maintained below 40° C. The reaction flask was rinsed with 470 mL of bromobenzene and 470 mL of water. The biphasic mixture was separated. The organic solution was concentrated under reduced pressure to about 820 mL. To this mixture was added 1320 mL of methyl tert-butyl ether, and 1790 mL of heptane. After crystallization has started, another 860 mL of heptane was added. The suspension was cooled to between 0–5° C., stirred for at least 30 min, and the filtered. The collected solid was washed with 530 mL of cold heptane, dried under vacuum at 40–50° C. to give 537 g of the ketone compound of Formula V, m.pt: 96.1° C.

Example 3

Preparation of Compound of Formula VI from a Compound of Formula V

A solution containing 293 g of the compound of Formula V, 336 g of 30% aqueous ethoxyamine solution, and 9 mL of acetic acid in 1170 mL of methanol was kept under reflux at about 65° C. for about 3 h. The reaction mixture was cooled to room temperature, and a solution of 450 mL of 25% sodium hydroxide was added. The biphasic mixture was vigorously stirred. After at least 10 min, the reaction mixture is added to a mixture of 1470 mL and 1470 mL of methyl tert-butyl ether. The layers were separated, and the organic layer was washed with 147 mL of water, followed by 147 mL of a 10% sodium chloride solution. The organic solution was concentrated to about 730 mL. The concentrate was diluted with 880 mL of methyl tert-butyl ether and concentrated again to about 730 mL. The distillation was repeated again with 880 mL of methyl tert-butyl ether, and the concentrate was used in the next step directly without additional purification.

Example 4

Preparation of Compound of Formula I from a Compound of Formula VI with Z-isomer Predominance Into a solution of the compound of Formula VI (600 mL of total solution including 247 g of active component in methyl tert-butyl ether as prepared in Example 3) was charged 758 mL of isopropyl alcohol ("IPA") and 2280 mL of methyl t-butyl ether ("MTBE"). An anhydrous IPA solution of HCl (4.8 N, 382 mL) was added dropwise. The resulting slurry was stirred for 12 h and then cooled to 0° C. After stirring 2 h, the crude product was filtered and washed with 200 mL of 1:2 of IPA and MTBE followed by 200 mL of MTBE. The resulting crude product was dried under vacuum at 55° C. for 2 days to give white solid (294 g, 92%). This crude product was found to contain 91:9 ratio of the E and Z-oximes respectively by HPLC analysis. The crude mixture was added into a 5 L round-bottomed flask followed by 1420 mL of IPA and 1420 mL of MTBE and then heated to 65° C. The resulting slurry was agitated by using mechanical stirrer for 68 h and then cooled to 10° C. After stirring 2 h, the final product was filtered and washed with 370 mL of 1:2 of IPA and MTBE followed by 370 mL of MTBE. The product of Formula I was dried under vacuum at 55° C. to give white solid (258 g, 90% yield, 96:4 ratio of E and Z-oxime respectively, by HPLC analysis). $^1$H NMR (400 MHz, DMSO-d6) the major product after isomerization (Z-oxime): δ 8.99 (bs, 2H), 7.63 (d, J=8.4, 2H), 7.27 (d, J=8.4, 2H), 3.99 (q, J=7.0, 2H), 3.24–3.21 (m, 2H), 2.90–2.84 (m, 3H), 1.85–1.82 (m, 2H), 1.71–1.64 (m, 2H), 1.12 (t, J=7.0, 3H); minor (E-oxime): δ 7.60 (d, J=8.4), 7.44 (d, J=8.4), 4.13 (q, J=7.0), 1.25 (t, J=7.0).

What is claimed is:

1. A process for preparing a compound of Formula VII:

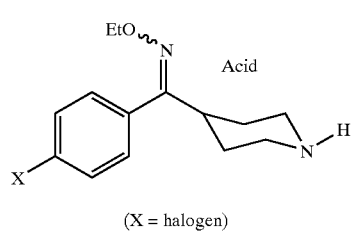

VII (X = halogen)

wherein said compound is in its Z-isomer form in at least about 90% stereochemical purity and "Acid" refers to acid salt, said process comprising:

(a) converting isonipecotic acid (Formula III) to its N-protected derivative (Formula IIIA):

where Y is a protecting group;
(b) converting the compound of Formula IIIA to its acid halide (Formula IV):

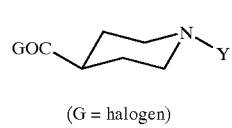

(G = halogen)

(c) reacting said compound of Formula IV with a suitable halobenzene in the presence of a suitable Friedel-Crafts catalyst to yield the compound of Formula V:

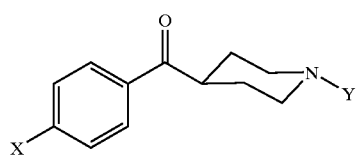

where X is a halogen;
(d) reacting the compound of Formula V with an alkoxyamine and an acid, to provide the compound of Formula VI as a mixture of the Z and E isomers:

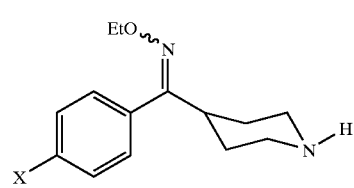

and
(e) isomerizing the compound of Formula VI by treatment with a strong acid and simultaneously converting to the desired acid salt of Formula VII with an enriched Z isomer, wherein the Z isomer predominates over the E-isomer by at least about a 90:10 ratio.

2. The process of claim 1, wherein X=Br, said "Acid" in Formula VII refers to hydrochloride, and Y is —C(O)CF$_3$, —C(O)CH$_3$, —C(O)OEt or —CHO.

3. The process of claim 2, wherein Y is —C(O)CF$_3$.

4. The process of claim 3, wherein said conversion in step (a) comprises reacting isonipecotic acid with trifluoroacetic anhydride in a solvent.

5. The process of claim 4, wherein said trifluoroacetic anhydride is employed in about 1–5 molar equivalent ratio with respect to said isonipecotic acid.

6. The process of claim 4, wherein said solvent is selected from the group consisting of toluene, xylene, chlorobenzene, methylene chloride, ethylene chloride, ethyl acetate, isopropyl acetate, n-butyl acetate, tetrahydrofuran and mixtures thereof.

7. The process of claim 6, wherein said solvent is isopropyl acetate.

8. The process of claim 1, wherein G in step (b) is chlorine, and said conversion comprises reacting the compound of Formula IIIA with an acid chloride.

9. The process of claim 7, wherein said chloride is selected from the group consisting of thionyl chloride, oxalyl chloride and phosphoryl chloride.

10. The process of claim 9, wherein said acid chloride is thionyl chloride.

11. The process of claim 10, wherein said thionyl chloride is employed in about 1–4 molar ratio with respect to said compound of Formula IIIA.

12. The process of claim 1, wherein in step (c), said halobenzene is selected from the group consisting of fluorobenzene, chlorobenzene, bromobenzene and iodobenzene, and said Friedel-Crafts catalyst is aluminum chloride.

13. The process of claim 12, wherein said halobenzene is bromobenzene.

14. The process of claim 13, wherein said bromobenzene is in about 1–5 molar equivalents with respect to the compound of the Formula IV.

15. The process of claim 14, wherein said aluminum chloride is present in about 1–6 molar equivalents with respect to the compound of Formula IV.

16. The process of claim 1, wherein said alkoxyamine in step (d) is ethoxyamine or ethoxyamine hydrochloride, said acid is acetic acid, and said reaction is performed in a solvent.

17. The process of claim 16, wherein said ethoxyamine or ethoxyamine hydrochloride is present in about 1–4 molar equivalents, with respect to the compound of Formula V.

18. The process of claim 17, wherein said solvent is selected from the group consisting of methanol, ethanol, isopropanol, n-butanol and mixtures thereof.

19. The process of claim 18, wherein said solvent is methanol.

20. The process of claim 1, wherein said strong acid in step (e) is HCl and said treatment of the compound of Formula VI comprises reacting with said strong acid in a solvent at about 10 to 80° C. for about 1–80 hours.

21. The process of claim 20, wherein said HCl is present in about 1–8 molar equivalents, with respect to the compound of Formula VI.

22. The process of claim 21, wherein said HCl is present in about 2–3 molar equivalents.

23. The process of claim 20, wherein said solvent is selected from the group consisting of ethanol, methanol, isopropanol, n-butanol, methyl tert-butyl ether, tetrahydrofuran, heptane, hexane, toluene, acetonitrile, benzonitrile and mixtures thereof.

24. The process of claim 23, wherein said solvent is a mixture of isopropyl alcohol and methyl tert-butyl ether.

25. A process for preparing a compound of the Formula:

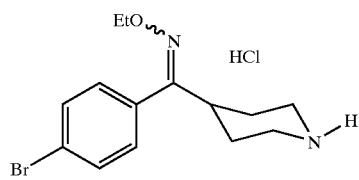

said process comprising:
(a) converting isonipecotic acid to a trifluoroacetyl compound of the Formula:

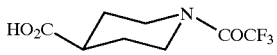

(b) converting the trifluoroacetyl compound in step (a) to its corresponding acid chloride of the Formula:

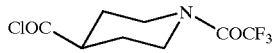

(c) reacting said acid chloride with bromobenzene in the presence of AlCl$_3$ to yield a bromo compound of the Formula:

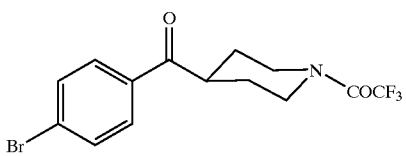

(d) converting the bromo compound of step (c) to an oxime of the Formula:

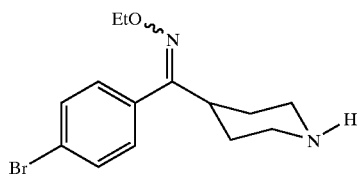

and (e) treating the oxime of step (d) with a strong acid under conditions suitable to result in the desired product of Formula I with at least about 90% stereochemical purity of its Z-isomer.

26. The process of claim 25, wherein said conversion in step (a) comprises reacting isonipecotic acid with trifluoroacetic anhydride in a solvent.

27. The process of step 26, wherein said solvent is isopropyl acetate.

28. The process of claim 27, wherein said trifluoroacetic anhydride is in about 1–5 molar equivalent ratio, with respect to said isonipecotic acid.

29. The process of claim 25, wherein said conversion in step (b) occurs by reacting the trifluoroacetyl compound of step (a) with thionyl chloride.

30. The process of claim 29, wherein said thionyl chloride is present in about 1–4 molar equivalents, with respect to said trifluoroacetyl compound of step (a).

31. The process of claim 25, wherein said bromobenzene in step (c) is present in about 1–5 molar equivalents, with respect to the acid chloride, and said aluminum chloride is present in about 1–6 molar equivalents, with respect to said acid chloride.

32. The process of claim 25, wherein said conversion in step (d) is performed by reacting said bromo compound with (i) ethoxyamine or ethoxyamine hydrochloride and (ii) and acetic acid, in a solvent.

33. The process of claim 32, wherein said ethoxyamine or ethoxyamine hydrochloride is present in about 1–4 molar equivalents, with respect to said bromo compound.

34. The process of claim 32, wherein said solvent is selected from the group consisting of methanol, ethanol, isopropanol, n-butanol and mixtures thereof.

35. The process of claim 25, wherein said strong acid in step (e) is HCl, and said treatment of the oxime comprises reacting said oxime with said strong acid in a solvent at about 10 to 80° C. for about 1–80 hours.

36. The process of claim 35, wherein said HCl is present about 1–8 molar equivalent ratio, with respect to said oxime.

37. The process of claim 36, wherein said solvent is selected from the group consisting of ethanol, methanol, isopropanol, n-butanol, methyl tert-butyl ether, tetrahydrofuran, heptane, hexane, toluene, acetonitrile, benzonitrile and mixtures thereof.

38. The process of claim 37, wherein said solvent is a mixture of isopropanol and methyl tert-butyl ether.

39. The process of claim 1, wherein said acid salt in step (e) is further reacted with a base to form a free base of the formula:

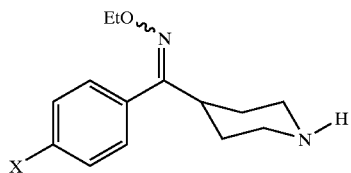

wherein said free base contains an enriched Z-isomer, with the Z-isomer predominating over the E-isomer by at least about a 90:10 ratio.

40. The process of claim 39, wherein X=Br.

* * * * *

UNITED STATES PATENT AND TRADEMARK OFFICE
CERTIFICATE OF CORRECTION

PATENT NO. : 6,914,142 B2
DATED : July 5, 2005
INVENTOR(S) : Wong, George S.K.

It is certified that error appears in the above-identified patent and that said Letters Patent is hereby corrected as shown below:

<u>Title page,</u>
Item [54], Title, "(4-BROMOPNENYL)" should be corrected to
-- (4-BROMOPHENYL) --.

Signed and Sealed this

Thirteenth Day of September, 2005

JON W. DUDAS
*Director of the United States Patent and Trademark Office*